United States Patent [19]

Madou et al.

[11] Patent Number: 5,368,704
[45] Date of Patent: Nov. 29, 1994

[54] MICRO-ELECTROCHEMICAL VALVES AND METHOD

[75] Inventors: Marc J. Madou, Palo Alto; Michael J. Tierney, San Jose, both of Calif.

[73] Assignee: Teknekron Corporation, Incline Village, Nev.

[21] Appl. No.: 103,274

[22] Filed: Aug. 6, 1993

[51] Int. Cl.⁵ ............................ C25F 3/00; C25F 7/00
[52] U.S. Cl. .................... 204/129.55; 204/224 M; 204/224 R; 204/252; 204/278; 204/279; 204/242; 204/129.7; 205/221; 205/223
[58] Field of Search ............ 204/129.55, 224 M, 248, 204/224 R, 279, 129.7, 242, 252, 278; 205/221, 223

[56] References Cited

U.S. PATENT DOCUMENTS

| | | | |
|---|---|---|---|
| 3,451,913 | 6/1969 | Laborde et al. | 204/248 |
| 3,554,890 | 1/1971 | Kariya | 204/224 M X |
| 4,069,121 | 1/1978 | Baud et al. | 204/129.55 X |
| 4,519,877 | 5/1985 | Wiech | 205/221 X |
| 4,535,518 | 8/1985 | Jaqua | 205/221 X |
| 4,765,864 | 8/1988 | Holland et al. | 156/644 |
| 4,874,500 | 10/1989 | Madou et al. | 204/412 |

OTHER PUBLICATIONS

Tierney et al., "Electroreleasing Composite Membranes for Delivery of Insulin and Other Biomacromolecules", *J. Electrochem. Soc.,* vol. 137, No. 6, pp. 2005–2006 (1990).

Tierney et al., "New Electrorelease Systems Based on Microporous Membranes", *J. Electrochem. Soc.* vol. 137, No. 12, pp. 3789–3793 (1990).

*Primary Examiner*—Donald R. Valentine
*Attorney, Agent, or Firm*—Schneck & McHugh

[57] ABSTRACT

A micromachined valve and valve array having one or more pores which are electrochemically opened and closed by dissolving and redepositing a barrier layer across a tiny opening or pore in substrate. The pore is spanned by two electrodes which apply a voltage to an electrolytic barrier layer material which dissolves in an electrolyte. Each open pore has a distinct flow rate related to its minimal cross-sectional area which together can form a binary sized array with each subsequent member in the array having a flow rate twice as large as the preceding member in the array. Any integral multiple of the smallest flow rate may be achieved by opening an appropriate combination of the pores with addressing logic. In a preferred embodiment, each bit in a binary representation of the desired flow rate acts as a switch for a pore having a flow rate corresponding to the bit position.

17 Claims, 2 Drawing Sheets

MICRO-ELECTROCHEMICAL VALVES AND METHOD

FIELD OF THE INVENTION

The invention relates generally to micromachined electrochemically controlled valves, and more particularly to a valve array for quantitatively controlling flow between two surfaces.

BACKGROUND OF THE INVENTION

In a large number of situations, it is desirable to be able to precisely control the flow rate of a liquid. Often, it is also desirable to modify the flow rate over time. For example, the therapeutic effect of many biologically active agents is critically dependent upon their circulating concentration in a patient. The therapeutic concentration range may be quite limited, with lower concentrations being ineffective and higher concentrations producing undesirable toxic effects.

Electrorelease is known in the art as a useful technique for electrochemically controlling the delivery of a chemical or drug. The delivery process can be controlled by switching the electrorelease system on and off, or by adjusting the rate of release. Electrorelease systems for small molecules are generally based on chemical entrapment of the molecule in a polymeric support.

*Journal of the Electrochemical Society* 137: 3789–3793 (1990) and references therein describe an electrorelease system for macromolecules based on microporous membranes. The molecule to be released is physically entrapped behind a composite membrane consisting of a microporous support membrane covered by a non-porous barrier layer. Release is initiated by electrochemically dissolving or disrupting the barrier layer. A thin metallic electrode, which does not seal the membrane's pores, is sandwiched between the microporous membrane and the non-porous barrier layer. The electrorelease rate is controlled by the number of pores which are electrochemically opened. The rate is modulated by limiting the amount of current passed during oxidation of the barrier layer or by separating the microporous membrane into individual electrorelease zones.

While it is possible to increase the electrorelease rate by opening more pores, the rate may not be decreased because the pores, once opened, cannot be closed. The resolution with which the release rate may be controlled is limited by the size of the separate electrorelease zones which may be constructed on the membrane surface and the number of pores within each zone.

It is therefore an object of the present invention to provide an improved electrorelease system for macromolecules which allows the electrorelease rate to be reduced or stopped.

It is a further object to provide an improved electrorelease system which has increased flow rate resolution.

SUMMARY OF THE INVENTION

Briefly, the present invention includes a monolithic substrate, such as a silicon wafer or plate, containing an array of variably sized holes. Each hole or pore has an associated electrode pair and is initially sealed with a material that can be electrochemically removed by applying a voltage to the associated electrode pair. The electrodes may either be located at the hole edge or along one wall of the rectangularly shaped holes. When the electrode is located at the hole edge, the sealing material will generally consist of a membrane layer which covers the hole. When the electrode is located on a passage wall, the barrier material will be located entirely within the passage as a film or plug. A common counter electrode may be located on one surface of the substrate or each individual passage may have a counter electrode located on a passage wall opposite the working electrode.

In a preferred embodiment, the barrier is composed of an electrolytic film material which may be repeatedly dissolved and redeposited in and from a compatible electrolyte to open and close the hole. Suitable materials include, for example, metals, such as silver or copper, or electroactive polymers, such as polypyrrole.

The flow rate through the substrate may be tailored to any desired value by opening the appropriate combination of holes. In a particularly preferred embodiment, a series of pores are used which have the property that each subsequent pore in the series has twice the flow rate of the previous pore in the series. The pore with the smallest flow rate defines the flow rate resolution of the system and any integral multiple of that flow rate may be achieved by an appropriate combination of open pores. The flow rates of the pores in the series correspond to the bit values in a binary representation of the desired flow rate. Each bit in the binary representation acts as a switch for the corresponding pore.

An advantage of the electrorelease system of the present invention is that the electrorelease rate may be reduced or stopped.

Another advantage is that the electrorelease system has increased flow rate resolution.

BEST MODE FOR CARRYING OUT THE INVENTION

Figure 1:
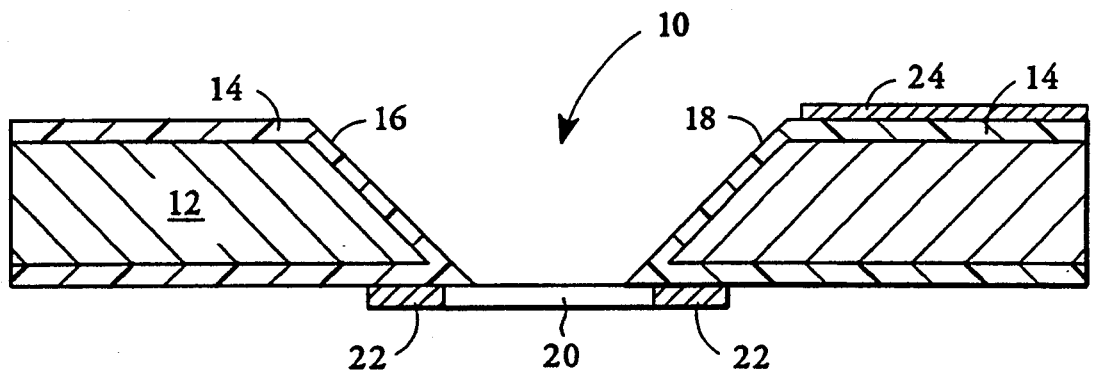
FIG. 1 is a side sectional view of an electrorelease pore covered by a silver membrane in accordance with an embodiment of the present invention.

With reference to FIG. 1, electrorelease hole or pore 10 is constructed in a monolithic substrate 12 using anisotropic etching techniques which are well known in the integrated circuit manufacturing arts and are described in detail in U.S. Pat. No. 4,765,864. Substrate 12 can be made of any of a number of materials although semiconductor materials such as silicon, silicon carbide, gallium arsenide, or the like are particularly advantageous when IC fabrication techniques are used. When substrate 12 is made of a semiconductor material, it is necessary to provide an appropriate insulating layer 14, such as silicon dioxide, to prevent electrical shorting through the substrate 12.

When produced by anisotropic etching, pore 10 is substantially rectangular in shape and has a pair of opposed slanted side walls 16 and 18 which are smooth and well defined. A thin membrane of electrolytic barrier material 20 covers the narrow end of pore 10. An electrode 22 is located at the edge of pore 10 completely surrounding and in contact with barrier 20. A counter electrode 24 is located on the surface of substrate 12 opposite to electrode 22 and barrier 20.

In operation, the surface of substrate 12 containing counter electrode 24 is in contact with an electrolyte which provides electrical communication between counter electrode 24 and electrode 22. Barrier material 20 is soluble in the electrolyte under an electromotive force. When a voltage difference is applied between counter electrode 24 and electrode 22 via external electrical leads, not shown, barrier 20 is electrochemically dissolved, allowing fluid flow through pore 10. Barrier 20 may be redeposited by applying a second voltage difference between electrode 22 and counter electrode 24. The magnitude and polarity of the second voltage must be determined experimentally for pores of various sizes and materials. A mere reversal of the polarity of the voltage difference between the electrodes may sometimes be sufficient, but in most instances different voltages may be required.

In one preferred embodiment, barrier 20 consists of a thin membrane of silver selectively deposited using the sacrificial layer technique described in U.S. Pat. No. 4,765,864. The electrolyte is a salt solution such as NaCl or KCl and the voltages involved are typically between $-1.5$ V and $+1.5$ V. When barrier 20 is composed of silver metal, a potential of $+0.7$ V vs. an Ag/AgCl reference electrode is sufficient to dissolve barrier 20. Larger potentials will, however, increase the rate of dissolution.

Figure 2:
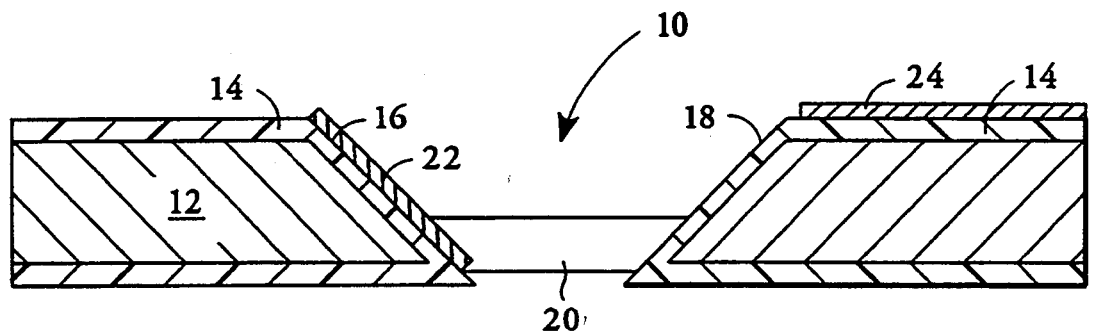
FIG. 2 is a side sectional view of an alternate embodiment of the present invention in which the electrode is located on the pore wall and the barrier material forms a plug entirely within the pore.

Referring now to FIG. 2, an alternate embodiment in which electrode 22 is located on side wall 16 and barrier 20 is located entirely within pore 10 is illustrated. In preferred embodiments, electrode 22 is deposited on passage wall 16 using lithographic techniques common in the integrated circuit and silicon micromachining arts. Barrier 20 is a film or plug of electroactive polymer material such as polypyrrole.

Figure 3:
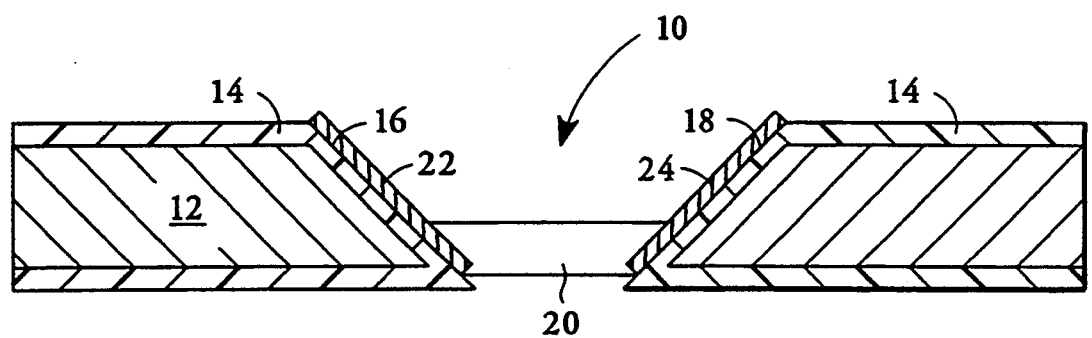
FIG. 3 is a side sectional view of a further alternate embodiment of the present invention in which the electrode and counter electrode are located on opposed walls within the pore.

Referring now to FIG. 3, an alternate preferred embodiment in which counter electrode 24 is located within pore 10 is illustrated. Counter electrode 24 is lithographically deposited on side wall 18 opposite to working electrode 22. A thin insulative layer 26 between barrier 20 and portions of the electrodes contacting the barrier prevents shorting of the electrodes.

Figure 4:
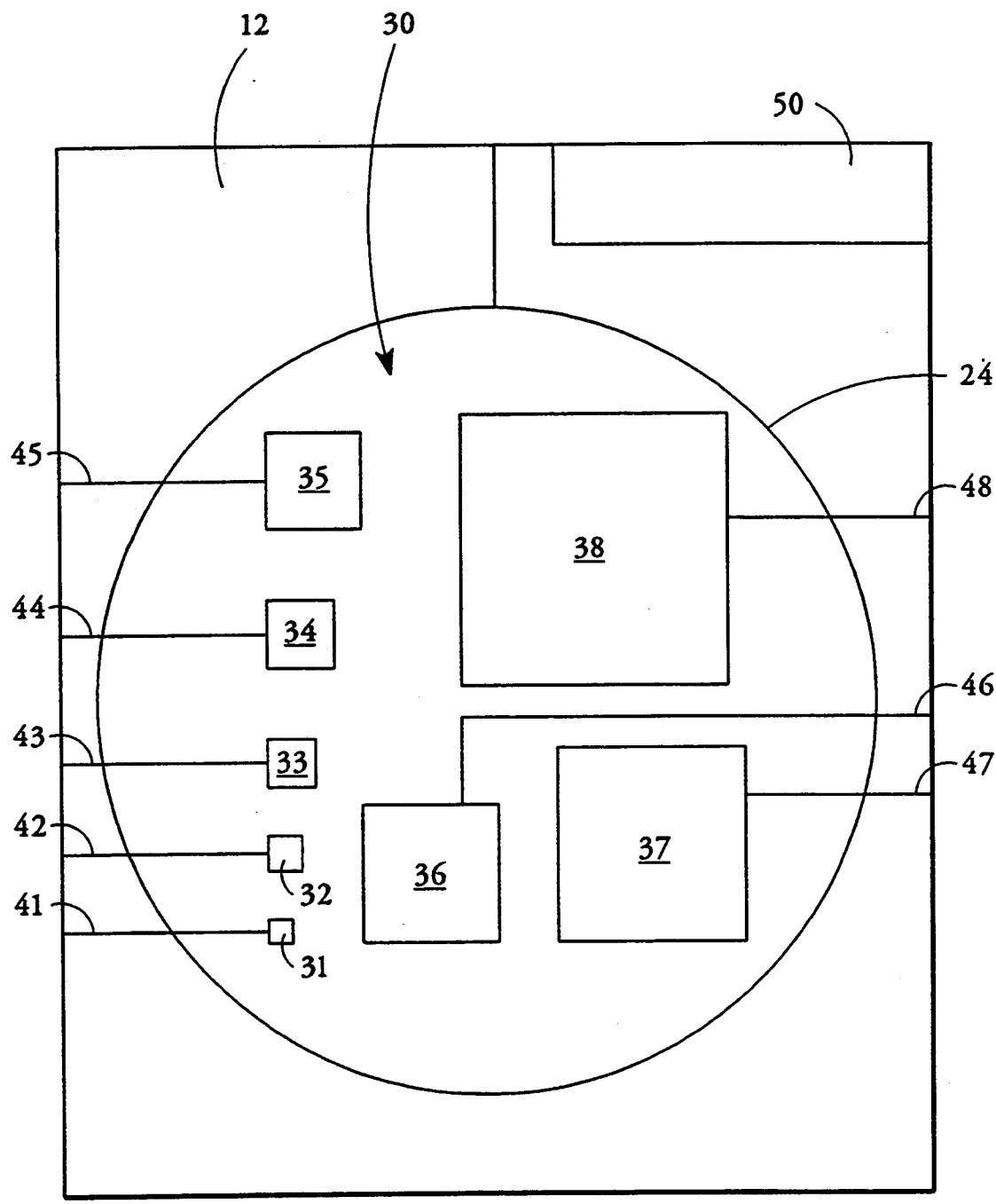
FIG. 4 is a plan view of a binary array of pores in accordance with the present invention.

FIG. 4 illustrates an array of 8 binary sized pores 31–38 surrounded by a common counter electrode 24. Each pore has an associated flow rate $F_i$, with $F_1$ being the flow rate of the smallest pore 31. The next largest pore 32 has a flow rate $F_2$, which is twice as large as flow rate $F_1$. Similarly, each subsequent pore in the series has a flow rate which is twice as large as the preceding number in the series. For example, pore 33 has a flow rate $F_3$ which is twice as large as $F_2$ and four times as large as $F_1$. In general, $F_i$ equals $2^{(i-1)} \times F_1$. Thus, pore 38 has the largest flow rate $F_8$ which is equal to $2^7 \times F_1$.

In operation, the smallest flow rate $F_1$ of pore 31 defines the flow resolution of array 30. Any integral multiple of flow $F_1$ between 1 and 255 ($2^8-1$) may be achieved by opening an appropriate combination of pores 31–38. Each pore 31–38 has a separate associated lead 41–48 which is in electrical communication with an integrated logic circuit 50. The desired flow rate is represented as a binary number stored in logic circuit 50 with each bit of the binary number acting as a switch for the corresponding pore in array 30. For example, inputting the binary number 10000010 opens pore 38 corresponding to the eighth bit and pore 32 corresponding to the second bit, resulting in a flow rate of $130 \times F_1$.

Increasing the number of pores N in the array increases the maximum flow rate $(2^N-1) \times F_1$. The flow resolution is increased by decreasing the size of the smallest pore. In general, the maximum flow rate is limited by the available surface area of substrate 12. The flow resolution is limited by the minimum sized pore which may be constructed. In practice, pore sizes ranging from about 1 micron to about 1 mm may be achieved using conventional integrated circuit manufacturing techniques. Use of a binary sized pore array minimizes the number of pores necessary to achieve any tailored flow rate within the resolution range of the array.

Valves made in accord with the present invention may be incorporated into drug delivery systems, such as infusion pumps, for controlled release of liquid drugs.

We claim:

1. A microelectrochemical valve structure comprising:

a monolithic substrate having a pair of opposed major surfaces;

an array of passages through said substrate, each of said passages extending between and connecting said major surfaces, each of said passages further having a size defined by its minimum cross-sectional area;

an electrochemically removable barrier associated with each of said passages in a position blocking fluid flow through said passage;

an electrode associated with each of said passages, said electrode being in contact with said passage barrier, said electrode further being in electrical communication with an external lead; and at least one counter electrode associated with one of said substrate major surfaces, said counter electrode being in electrical communication with an external lead, said counter electrode further having the property of being in electrical communication with said passage electrodes when said associated substrate surface is in contact with an electrolyte, wherein a voltage difference applied between said counter electrode lead and one of said passage electrode leads removes the barrier associated with said passage thereby increasing flow communication between said substrate surfaces by an amount proportional to said passage's size.

2. The structure of claim 1 wherein said passage barrier comprises a membrane layer deposited on one of said substrate major surfaces covering the opening of said associated passage.

3. The structure of claim 1 wherein said passage barrier comprises a plug located entirely within said associated passage.

4. The structure of claim 1 wherein said passage barrier is dissolved when said voltage difference is applied.

5. The structure of claim 4 wherein said passage barrier is redeposited when a second voltage difference is applied.

6. The structure of claim 1 wherein said passage barrier is physically displaced by the evolution of gas at said passage electrode when said voltage difference is applied.

7. The structure of claim 1 wherein said array of passages includes a series of n passages, each of said passages in said series having a different size, said series being characterized by the first member of said series having the smallest size and each successive member of said series having a size twice the size of the previous member such that the nth member of said series has a size $2^{(n-1)}$ times the size of the first member of said series.

8. A method for producing quantitatively variable flow communication between major surfaces of a monolithic substrate comprising:
forming a series of n passages through said substrate, each of said passages having a different size defined by its minimum cross-sectional area, said series being characterized by the first member in said series having the smallest size with each subsequent member in said series having a size twice as large as the previous member such that the nth member of said series has a size $2^{(n-1)}$ times the size of the first member;
positioning a separate electrochemically removable barrier to block flow through each of said passages, each of said barriers being selectively removable; and
electrochemically removing said barriers from a selected group of said passages to produce quantitative flow communication between substrate surfaces.

9. The method of claim 8 wherein said barriers are electrochemically removed by establishing a potential difference between an electrode in contact with said barrier and a counter electrode in electrical communication with said barrier electrode via an electrolyte.

10. The method of claim 9 wherein said barrier is removed by the evolution of gas at said barrier electrode.

11. The method of claim 9 further characterized by replacing a selected portion of said removed barriers to quantitatively reduce said flow communication between said substrate surfaces.

12. The method of claim 11 wherein said removed barriers are replaced by applying a second voltage difference.

13. The method of claim 12 wherein said barrier is removed by dissolving the material composing said barrier and replaced by redepositing said barrier material.

14. The method of claim 8 wherein the size of said smallest passage defines a minimum non-zero flow communication between said surfaces and any integral multiple of said minimum flow communication can be produced by opening a selected group of said passages, said group being selected to correspond to the binary representation of said integral multiple.

15. A system for producing quantitative variable flow through a monolithic substrate comprising:
an array of n individually gated passages through said substrate, each of said passages having a different predetermined flow rate $f_i$ associated therewith when said passage gate is open, said flow rates being characterized by the relation $f_i = 2^{(i-1)} \times f_1$ for i=1 to n with $f_1$ being the smallest flow rate;
input means for expressing a desired flow rate as in n-bit binary numbers; and
means for selectively opening the passage through said substrate having flow rate $f_i$ when the ith bit in said binary number is a 1.

16. The system of claim 15 wherein each of said passages is gated by an electrochemically removable barrier positioned to block flow through said passage, said barrier being in contact with an electrode in electrical communication with an external lead, said barrier electrode further being in electrical communication with a counter electrode via an electrolyte.

17. The system of claim 16 wherein said selective opening means includes switch means for connecting said barrier electrode leads to a voltage source, said switch means connecting the barrier electrode lead corresponding to the passage having flow rate $f_i$ to said voltage source when the ith bit in said binary number is a 1.

* * * * *